United States Patent [19]

McAuliffe et al.

[11] 4,251,452
[45] Feb. 17, 1981

[54] MANGANESE (II) COMPLEXES

[75] Inventors: Charles A. McAuliffe, Altrincham; William Levason, Southampton; Francis P. McCullough, Cheadlehulme, all of England

[73] Assignee: National Research Development Corporation, London, England

[21] Appl. No.: 16,081

[22] Filed: Feb. 28, 1979

[30] Foreign Application Priority Data

Mar. 3, 1978 [GB] United Kingdom ............... 08547/78
Sep. 25, 1978 [GB] United Kingdom ............... 37949/78

[51] Int. Cl.$^3$ ............................................. C07F 13/00
[52] U.S. Cl. ................................ 260/429 R; 423/210
[58] Field of Search ..................................... 260/429 R

[56] References Cited

U.S. PATENT DOCUMENTS

| | | | |
|---|---|---|---|
| 3,355,439 | 11/1967 | Welch et al. | 260/429 R X |
| 3,438,805 | 4/1969 | Potrafke | 260/429 R X |
| 4,012,399 | 3/1977 | Hechenbleikner et al. | 260/429 R X |

OTHER PUBLICATIONS

Chemical Abstracts, 67 60439t, (1967).
Chemical Abstracts, 56 13783b, (1962).
Chemical Abstracts, 81 20255a, (1974).
Chemical Abstracts, 70 116182k, (1969).

*Primary Examiner*—Helen M. S. Sneed
*Attorney, Agent, or Firm*—Oblon, Fisher, Spivak, McClelland & Maier

[57] ABSTRACT

Compounds of formula I are useful in the separation of a gas such as oxygen, hydrogen, sulphur dioxide, alkenes and carbon monoxide from a fluid comprising the gas.

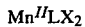

$$Mn^{II}LX_2 \qquad I$$

In formula I:L represents a monodentate ligand of formula IA and X is a species capable of existing as an anion

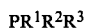

$$PR^1R^2R^3 \qquad Ia$$

wherein $R^1$, $R^2$ and $R^3$ which may be identical or different represent substituted or unsubstituted alkyl, cycloalkyl or aryl groups or hydrogen and X represents —Cl, —Br, —I, —CN, —NO$_2$, —NO$_3$, —OH, —NCS or —NCO provided that no more than two of the groups $R^1$, $R^2$ and $R^3$ are substituted or unsubstituted aryl groups and that at least one of the groups $R^1$, $R^2$ and $R^3$ is a substituted or unsubstituted alkyl, cycloalkyl or aryl group.

9 Claims, No Drawings

MANGANESE (II) COMPLEXES

This invention relates to the sorption of gases and finds application in the purification of gases, in particular the purification of nitrogen by removal of traces of oxygen and in the production of oxygen from air.

It is known that certain metal complexes take up gases to form adducts from which the gases can be recovered. The Cobalt (II) complex known as the Salen Chelate and related Fluomine chelate complexes of the Vaska type, in which the metal is iridium, ruthenium, osmium or rhodium, take up oxygen reversibly. Under moderate conditions the adducts do not however release oxygen to regenerate the sorbent complexes sufficiently readily to enable oxygen to be produced or nitrogen to be purified on a commercial scale.

Complexes have now been found which take up gases to form adducts from which the gases can be readily recovered.

Accordingly, the present invention comprises a compound of formula I, $$Mn^{II}LX_2 \qquad \qquad I$$

where L represents a monodentate ligand of formula IA $$PR^1R^2R^3 \qquad \qquad IA$$

in which formula, $R^1$, $R^2$ and $R^3$, which may be identical or different, represent substituted or unsubstituted alkyl, cycloalkyl or aryl groups or hydrogen and $X$ which is a species capable of existing as an anion represents —Cl, —Br, —I, —CN, —$NO_2$, —$NO_3$, —OH, —NCS or —NCO provided that no more than two of the groups $R^1$, $R^2$ and $R^3$ are substituted or unsubstituted aryl groups and that at least one of the groups $R^1$, $R^2$ and $R^3$ is a substituted or unsubstituted alkyl, cycloalkyl or aryl group.

Also included within the scope of the present invention is a method of separating a gas from a fluid comprising the gas wherein the fluid, which is generally gaseous, is treated with a compound of formula I so that the gas is sorbed by the compound.

Compounds according to the present invention may exist in dimeric or tetrameric form in which case whilst the empirical formulae is $Mn^{II}LX_2$ the molecular formulae are $(X)(L) Mn\, X_2\, Mn(X)(L)$ and $X_2\, Mn(X)(L)\, Mn\, X_2\, Mn(L)(X)\, Mn\, X_2$ Although, as it will be appreciated, the species X in the compound of formula I may be selected from a range of atoms or groups capable of existing in anionic form, the halogens Cl, Br and I and isothiocyanate are preferred as compounds thereof show particularly rapid rates of oxygen uptake.

In general, it is preferred for each of the groups $R^1$, $R^2$ and $R^3$ to represent a substituted or unsubstituted alkyl, cycloalkyl or aryl group and for at least one of the groups $R^1$, $R^2$ and $R^3$ to represent a radical of formula —$CH_2R^a$ where $R^a$ represents hydrogen or a substituted or unsubstituted alkyl or cycloalkyl group. When the group $R^a$ is a substituted alkyl group, the substituent is generally carried on a carbon atom which is spaced from phosphorus by at least two carbon atoms, and the alkyl group preferably comprises at least four carbon atoms and preferably no more than ten carbon atoms in a chain. The alkyl group may be substituted by one or more aryl groups in which case it is preferable for such an aryl group to carry at least one electron donating substituent such as an alkyl group. The group $R^a$, when present, may be an unsubstituted alkyl or cycloalkyl group, for example a branched alkyl group. It is however preferred that the group $R^a$ is a straight chain alkyl group containing at least one and preferably no more than ten carbon atoms.

When one or more of the groups $R^1$, $R^2$ and $R^3$ is an aryl group, the aromatic ring in the group preferably carries one or more electron donating substituent, typically an alkyl substituent.

Ligands of particular interest include those of the following formulae wherein Cy represents: cyclohexyl and Pn represents: n-pentyl and R represents: Me, Et, $Pr^n$, $Pr^i$, $Bu^n$, $Bu^i$, Pn:

$PhPR_2$, $Ph_2PR$, $CyPR_2$, $Cy_2PR$, $PR_3$, $MePR_2$, $EtPR_2$, $Pt^nPR_2$, $Bu^nPR_2$, $PPh_2H$. The ligands $PMe_3$, $PEt_3$, $PPr_3^n$, $PPr_3^i$, $PBu_3^n$, $PBu_3^i$, $PEt_2Me$, $PEtMe_2$, $PPhMe_2$, $PPhEt_2$, $PPh_2Me$, $PPh_2Et$ and $PPh_2H$ are of especial interest.

Compounds of formula I may be used to take up various gases such as oxygen, hydrogen, sulphur dioxide, alkenes, e.g. ethylene and carbon monoxide from fluids containing one or more of the gases. As hereinbefore indicated however, the compounds find particular application in the removal of trace amounts of oxygen from gases such as nitrogen and in the production of oxygen from air. For the former application it is preferred that X be Cl, Br or I and for the ligand L to be $L^1$ which represents $PPhMe_2$, $PPhEt_2$, $PMe_3$, $PEt_3$, $PPr_3^n$, $PPr_3^i$, $PBu_3^n$ or $PBu_3^i$. For the latter application however it is generally preferred that X be isothiocyanate as compounds such as $Mn(NCS)_2\, Bu_3^nP$ can be used to sorb and desorb oxygen at pressures near ambient. When X is isothiocyanate the ligand L is preferably one of the group $L^1$. Compounds in which X represent Cl, Br or I are also however of interest for use in the production of oxygen from air and in this case it is preferred for the ligand L to be $PPh_2Me$ or $PPh_2Et$ or $PPhEt_2$ (e.g. $PPhEt_2MnBr_2$). The present invention allows oxygen which is substantially free from inert gases as argon to be recovered from air.

Compounds from formula I may be prepared by treating an appropriate manganese (II) salt with the ligand, preferably in a solvent, subsequent removal of which yields an oil or crystalline solid which changes colour on uptake of oxygen from air from a pale colour to an intense green, blue, purple or pink hue for example. Because of the reactivity of the ligand molecules towards oxygen, the ligand is in practice usually manipulated in oxygen-free conditions for example under nitrogen. It is moreover generally necessary for the preparation to be conducted under rigorously anhydrous conditions using starting materials which have been thoroughly dried before use. The manganese salts in particular are preferably dehydrated by prolonged heating in vacuo.

The solvent employed, which in general is thoroughly dehydrated before use, may be one which adequately dissolves the reactants whilst co-ordinating insufficiently strongly with the manganese to prevent reaction from proceeding. Alternatively, however, the solvent may be one in which the salt is substantially insoluble but nevertheless reacts with the ligand to one of the present compounds. Hydroxylic solvents are generally undesirable but ethereal and aromatic hydrocarbon solvents such as tetrahydrofuran, 1,4-dioxan and toluene are normally suitable. Although the range of solvents available for use in the preparation of the present compounds is limited, the range of solvents into which the compounds may be transferred for use, once formed, is larger and includes chloroform for example. The choice of solvent may however have a pronounced effect on the activity of at least certain compounds according to the present invention.

It is highly desirable that the method of separating the gas from the fluid be operated under strictly anhydrous conditions so that the risk of decomposition of the compound is minimised.

Although, moreover, many of the present compounds are remarkably robust and withstand a great number of sorption-desorption cycles without decomposition, it is preferable, at least for certain compounds, that the amount of gas, for example oxygen, available to the compounds is controlled in order to reduce the risk or irreversible deactivation thereof.

In practice the present compounds are preferably distributed on the surface of a support material, for example a mass of glass beads, during contact with the gas-containing fluid, which fluid is typically itself gaseous, so that the surface area accessible to the fluid is relatively increased.

Gases are in general conveniently removable from adducts with the present compounds by adjustment of the external pressure. In a typical system suitable for the production of oxygen from air, a mass of particulate support material carrying the active compound, e.g. a bed thereof, in a container provided with an inlet for fluid, is treated with pressurised fluid containing oxygen. Oxygen is removed from the fluid by the compound, the residual fluid is separated from the support material carrying the active compound and oxygen is recovered therefrom by a relative reduction in pressure. The cycle may then be repeated with the deoxygenated compound. Alternatively, a solution containing the active compound may be pressurised and pumped into a vessel packed with a particulate material through which a gaseous fluid containing oxygen, such as air, is passed under pressure preferably in countercurrent flow thereto. Oxygen transfers from the fluid to this solution which then passes into a chamber in which the pressure is relatively decreased, for example to atmospheric. Oxygen boils out and may be recovered and the residual solution is used in further repetitions of the cycle.

Although sorption of gases by compounds of formula I proceeds at an appreciable rate in the dark it has unexpectedly been found that sorption, particularly of oxygen, is accelerated by light, for example by light from the sun or from tungsten or fluorescent lamps. In many cases such irradiation also increases the capacity and sensitivity of the compounds with respect to the gas. It is therefore generally preferable for the present compound to be subjected to sunlight or artificially irradiated during gas uptake.

In general as the temperature of the sorbent compound is lowered the capacity thereof for gas increases but the rate of desorption decreases. Operating temperatures usually reflect a compromise between these factors but for guidance temperatures generally are in the range 0°-50° C.

The present invention also includes within its scope an adduct of a gas with a compound of formula I, from which adduct the latter compounds may be regenerated by removal of the gas, e.g. by reduction in pressure. Such compounds are considered to have the formula Mn L $X_2$ Y wherein Y represents one or more molecules of a gas such as $H_2$, $SO_2$, CO or an alkene, e.g. ethylene or one molecule of oxygen.

The method of the present invention may be employed for the purification of gases such as nitrogen, by passing the gas through the compound of formula I carried on a particulate support. The compound carried on a particulate support, when used in this method is typically contained in a tubular vessel provided with a gas inlet and an inlet. When spent, the compound may be reactivated by heat treatment or subjection to reduced pressure or discarded.

The invention is illustrated by the following Examples.

EXAMPLES 1-6

Preparation of Compounds $Mn^{II}LX_2$ (X=Cl, Br or I)

Anhydrous manganese (II) halides (Mn $X_2$, X=Cl, Br, or I are prepared by heating the commercial hydrated salts in vacuo at 150°-300° C./1 mm Hg for 12 hours. The products are pale pink solids which are powdered and manipulated in a dry box (they rapidly absorb moisture from air). Tetrahydrofuran is dried by refluxing over sodium wire, and freshly distilled from sodium benzophenone ketyl under nitrogen.

Ligands are prepared by the method described in L. Maier, "Organic Phosphorus Compounds," Vol. 1, p. 1, (Wiley & Sons 1972) and by methods described in the reference therein. The ligands are purified by distillation in vacuo where liquid or recrystallisation where solid.

The air-sensitive nature of many of the ligands requires that they are generally handled under nitrogen and by syringe techniques.

0.002 mol anhydrous manganese (II) chloride (0.252 g), bromide (0.430 g), or iodide (0.618 g) is dissolved in dry tetrahydrofuran (50 $Cm^3$) under an oxygen-free nitrogen atmosphere and x mol of the ligand L is added via a syringe. After stirring for 30 minutes, the solvent is removed under reduced pressure to yield a colourless oil or semi-solid.

On exposure to air the compounds take up oxygen, changing colour as shown in Table I, which also records the amount of ligand used for reaction with 0.002 mol of the manganese halide.

TABLE I

| Example | Ligand | Amount of ligand mol. | Amount of ligand g. | Colour of Compound | Colour of Adduct |
|---|---|---|---|---|---|
| 1 | $PMe_3$ | | | | |
| 2 | $PEt_3$ | 0.002 | 0.216 | colourless or very pale yellow | blue-purple |
| 3 | $P(n-C_3H_7)_3$ | 0.002 | 0.320 | | |
| 4 | $P(n-C_4H_9)_3$ | 0.002 | 0.404 | | |
| 5 | $PMe_2Ph$ | 0.002 | 0.266 | | |
| 6 | $P(i-C_3H_7)_3$ | 0.002 | 0.320 | | |

Removal of oxygen by reducing the pressure in the vessel containing the compound of formula I results in reversal of the colour change indicating regeneration of the compound.

A stream of nitrogen passes through a solution of the compound of formula I in tetrahydrofuran returns the solution to its former colour at a rapid rate. Exposure to oxygen produced an intense colour. The cycle is repeatable at least five times.

EXAMPLE 7

Oxygen Uptake Isotherm Data

Compound: $MnBr_2(Me_2PPh)$ (M.W.=352.84). Sample wt.=7.3 mg (0.02 mmol.)

Total uptake $O_2$=0.08 mg t=21° C. (1:1 requires 0.66 mg (12%)

| Partial Pressure $O_2$ (torr) | Wt. increase (mg) |
| --- | --- |
| 0.5 | 0 |
| 0.75 | 0 |
| 1.0 | 0 |
| 2.0 | 0 |
| 3.0 | .01 |
| 6.0 | .03 |
| 9.0 | .04 |
| 14 | .05 |
| 18 | .06 |
| 21 | .08 |
| 23 | .08 |
| 25 | .08 |
| 100 | .08 |

EXAMPLE 8

Oxygen Uptake Isotherm Data

Compound: $MnI_2(Me_2PPh)$ (M.W.=446.88). Sample wt.=20.0 mg (0.045 mmol). Total Uptake $O_2$=0.05 mg t=24° C. (1:1 requires 1.4 mg (3.5%))

| Partial Pressure $O_2$ (torr) | Wt. increase (mg) |
| --- | --- |
| 0.4 | 0 |
| 0.75 | 0 |
| 1.0 | 0 |
| 3.0 | 0 |
| 6.0 | 0 |
| 9.0 | .01 |
| 12 | .015 |
| 17 | .02 |
| 21 | .03 |
| 25 | .035 |
| 31 | .045 |
| 36 | .05 |
| 41 | .05 |
| 46 | .05 |
| 100 | .05 |

EXAMPLE 9

Oxygen Uptake Isotherm Data

Compound: $MnI_2(Pr_3{}^nP)$ (M.W.=468.97) Sample wt.=18.4 mg (0.039 mmol).

Total uptake $O_2$=2 mg t=15° C. (1:1 requires 1.26 mg (16%))

| Partial Pressure $O_2$ (torr) | Wt. increase (mg) |
| --- | --- |
| 0.5 | 0 |
| 1.0 | 0 |
| 2.0 | 0 |
| 3.0 | 0 |
| 4.0 | 0 |
| 5.0 | .02 |
| 6.0 | .059 |
| 11 | .14 |
| 18 | .18 |
| 20 | .20 |
| 23 | .20 |
| 100 | .20 |

EXAMPLE 10

Oxygen Uptake Isotherm Data

Compound: $MnBr_2(Et_2PPh)$ (M.W.=380.9) Sample wt.=18.0 mg (0.047 mmol)

Total uptake $O_2$=1.0 mg t=27° C. (1:1 requires 1.51 mg (7%))

| Partial Pressure $O_2$ (torr) | Wt. Increase (mg) |
| --- | --- |
| 0.3 | 0 |
| 0.7 | 0 |
| 1.0 | 0 |
| 2.0 | 0 |
| 3.0 | .01 |
| 5.0 | .02 |
| 7.0 | .03 |
| 9.0 | .04 |
| 14 | .06 |
| 19 | .08 |
| 22 | .09 |
| 26 | 0.1 |
| 27 | 0.1 |
| 100 | 0.1 |

EXAMPLE 11

Preparation of $Mn(NCS)_2(Bu_3{}^nP)$

Manganese (II) thiocyanate is prepared from manganese sulphate and barium thiocyanate and recrystallised from alcohol. The thiocyanate is dried as described above for manganese halides and is used for preparation of $Mn(NCS)_2(Bu_3{}^nP)$ by the method described in Examples 1 to 6.

Oxygen Sorption Data

Sample Weight: 40 mg (lump)
$t_1$: 41° C.  $t_2$: 18° C.

| Partial Pressure $O_2$ (torr) | Weight Increase (mg) | |
| --- | --- | --- |
| | $t_1$ | $t_2$ |
| 10 | 0.0 | 0.0 |
| 32 | 0.0 | 0.0 |
| 50 | 0.0 | 0.0 |
| 70 | 0.0 | 0.0 |
| 76 | 0.0 | 0.0 |
| 170 | 0.01 | 0.14 |
| 220 | 0.01 | 0.14 |
| 760 | 0.01 | 0.14 |

EXAMPLE 12

Sorption of $SO_2$ by $MnBr_2(Pr_3{}^nP)$

Sample Weight: 23.0 mg. (0.0613 mmole)
t=19° C.

Total $SO_2$ uptake=1.38 mg. (1:1 requires 3.92 mg (35.2%))

| $pSo_2$ (torr) | Weight increase (mg) |
| --- | --- |
| 0.4 | 0 |
| 34 | 0.04 |
| 49 | 0.12 |
| 68 | 0.20 |
| 83 | 0.27 |
| 93 | 0.33 |
| 106 | 0.40 |
| 121 | 0.49 |
| 136 | 0.57 |
| 155 | 0.69 |
| 163 | 0.78 |

-continued

| pSO$_2$ (torr) | Weight increase (mg) |
| --- | --- |
| 178 | 0.91 |
| 193 | 1.06 |
| 207 | 1.22 |
| 227 | 1.38 |

EXAMPLE 13

Sorption of H$_2$ by MnBr$_2$P(Me$_2$Ph)

Sample Weight: 54.0 mg
t=21° C.

| pH$_2$ (torr) | Weight Increase (mg) |
| --- | --- |
| 0.01 | 0.00 |
| 0.10 | 0.00 |
| 10 | 0.01 |
| 50 | 0.02 |
| 75 | 0.025 |
| 100 | 0.025 |

EXAMPLE 14

Sorption of Ethylene by MnBr$_2$P(Me$_2$Ph)

Sample Weight: 54.0 mg
t=21° C.

| pC$_2$H$_4$ (torr) | Weight Increase (mg) |
| --- | --- |
| 0.0 | 0.0 |
| 0.1 | 0.0 |
| 12 | 0.015 |
| 30 | 0.030 |
| 36 | 0.035 |
| 40 | 0.035 |

What is claimed is:

1. A compound of the formula I, $$Mn^{II}LX_2 \qquad I$$

wherein L represents a monodentate ligand of the formula IA, $$PR^1R^2R^3 \qquad II$$

in which formula R$^1$, R$^2$ and R$^3$, which may be identical or different, represent alkyl, cycloalkyl, or aryl groups or hydrogen, provided that no more than two of the groups R$^1$, R$^2$ and R$^3$ are aryl groups and that at least one of the groups R$^1$, R$^2$ and R$^3$ is an alkyl, cycloalkyl or aryl group; and wherein X which is a species capable of existing as an anion, represents —Cl, —Br, —I, —CN, —NO$_2$, —NO$_3$, —OH, —NCS or —NCO.

2. A compound according to claim 1, characterised in that X represents Cl, Br, I or NCS.

3. A compound according to claim 1, characterised in that none of the groups R$^1$, R$^2$ and R$^3$ represents hydrogen.

4. A compound according to claim 1, characterised in that at least one of the groups R$^1$, R$^2$ and R$^3$ represents a radical of formula —CH$_2$R$^a$ wherein R$^a$ represents hydrogen or a alkyl or cycloalkyl group.

5. A compound according to claim 4, characterised in that the radical R$^a$ represents a straight chain alkyl group comprising no more than ten carbon atoms.

6. A compound according to claim 1, characterised in that L represents Ph PR$_2$, Cy PR$_2$, Ph$_2$ PR, Cy$_2$ Pr, PR$_3$, Me PR$_2$, EtPR$_2$, Pr$^n$ PR$_2$, Bu$^n$ PR$_2$ or PPh$_2$H wherein Cy represents cyclohexyl, R represents Me, Et, Pr$^n$, Pr$^i$, Bu$^n$, Bu$^i$ or Pn, Pn representing n-pentyl.

7. A compound according to claim 6, characterised in that L represents PMe$_3$, PEt$_3$, PPr$_3^n$, Pr$^i_3$, PBu$_3^n$, PBu$^i_3$, PEt$_2$ Me, PEt Me$_2$, PPh Me$_2$, PPhEt$_2$, PPh$_2$ Me or PPh$_2$ Et.

8. A compound according to claim 7, characterised in that the compound has the formula MnPMe$_3$X$_2$, MnP Et$_3$ X$_2$, MnP Pr$_3^n$X$_2$, MnPPr$_3^i$X$_2$, MnP Bu$_3^n$X$_2$, MnP Me$_2$ PhX$_2$, MnP Et$_2$ PhX$_2$ wherein X represents Cl, Br or I, or Mn PBu$_3^n$ (NCS)$_2$.

9. A process for the preparation of a gas sorbent compound of the formula I, $$Mn^{II}LX_2 \qquad I$$

comprising: reacting a monodentate ligand of the formula IA $$PR^1R^2R^3 \qquad IA$$

in which formula R$^1$, R$^2$ and R$^3$, which may be identical or different, represent alkyl, cycloalkyl, or aryl groups or hydrogen, provided that no more than two of the groups R$^1$, R$^2$ and R$^3$ are aryl groups and that at least one of the groups R$^1$, R$^2$ and R$^3$ is an alkyl, cycloalkyl or aryl group; with an anhydrous salt of the formula $$Mn^{II}X_2$$

in which formula X, which is a species capable of existing as an anion, represents —Cl, —Br, —I, —CN, —NO$_2$, —NO$_3$, —OH, —NCS or —NCO; under anhydrous conditions; and in the absence of oxygen.

* * * * *

UNITED STATES PATENT AND TRADEMARK OFFICE
CERTIFICATE OF CORRECTION

PATENT NO. : 4,251,452

DATED : February 17, 1981

INVENTOR(S) : CHARLES ANDREW AcAULIFFE ET AL

It is certified that error appears in the above—identified patent and that said Letters Patent is hereby corrected as shown below:

Column 1, lines 48-49, delete "$X_2Mn(X)(L)MnX_2Mn(L)(X)-MnX_2$" and insert --$LX_2Mn(X)(L)MnX_2Mn(L)(X)MnX_2L$--.

Column 2, line 17, delete "$Pt^nPR_2$" and insert --$Pr^nPR_2$--.

Column 2, line 44, after "Compounds", delete "from" and insert --of--.

Column 4, line 10, delete "inlet" (second occurrence) and insert --outlet--.

Column 4, line 28, after "Maier" insert -- and G.M. Kosolapoff--.

Column 8, line 21, delete "$Pr^i_3$" and insert --$PPr^i_3$--.

Signed and Sealed this

Second Day of March 1982

[SEAL]

Attest:

GERALD J. MOSSINGHOFF

Attesting Officer      Commissioner of Patents and Trademarks